United States Patent [19]

Foscante et al.

[11] Patent Number: 4,670,481
[45] Date of Patent: Jun. 2, 1987

[54] ORGANOTIN ACRYLATE AND ORGANOTIN POLYSILOXANE ANTIFOULING COATING COMPOSITION

[75] Inventors: Raymond E. Foscante, Yorba Linda; Charles D. Stevens, Long Beach; Lee M. Parson, Inglewood, all of Calif.

[73] Assignee: Ameron, Inc., Monterey Park, Calif.

[21] Appl. No.: 829,505

[22] Filed: Feb. 14, 1986

[51] Int. Cl.$^4$ .............. A01N 9/00; C08G 77/04; C09D 5/16; C09D 5/38

[52] U.S. Cl. .................. 523/122; 523/177; 524/413; 524/431; 524/432; 524/451; 525/185

[58] Field of Search .............. 523/122, 177; 524/413, 524/431, 432, 451; 525/185

[56] References Cited

U.S. PATENT DOCUMENTS

| | | | |
|---|---|---|---|
| 3,167,473 | 1/1965 | Leebrick | 167/38.6 |
| 3,979,354 | 9/1976 | Dyckman et al. | 526/317 |
| 4,021,392 | 5/1977 | Milne et al. | 427/409 |
| 4,025,693 | 5/1977 | Milne | 428/907 |
| 4,064,338 | 12/1977 | Russell | 526/230 |
| 4,080,190 | 3/1978 | Law et al. | 523/177 |
| 4,082,709 | 4/1978 | Dyckman et al. | 106/15 R |
| 4,098,971 | 7/1978 | Philip et al. | 526/240 |
| 4,130,466 | 12/1978 | Kramer | 428/470 |
| 4,139,515 | 2/1979 | Dennington | 106/15.05 |
| 4,157,999 | 6/1979 | Matsuda et al. | 428/907 |
| 4,174,339 | 11/1979 | Matsuda et al. | 523/177 |
| 4,191,579 | 3/1980 | Hails et al. | 106/15 R |
| 4,260,535 | 4/1981 | Russell | 525/201 |
| 4,385,134 | 5/1983 | Foscante et al. | 523/177 |
| 4,485,197 | 11/1984 | Yokoi et al. | 523/177 |
| 4,532,269 | 7/1985 | Gitlitz et al. | 523/122 |
| 4,576,838 | 3/1986 | Rosen et al. | 523/122 |

*Primary Examiner*—Herbert J. Lilling
*Attorney, Agent, or Firm*—Christie, Parker & Hale

[57] ABSTRACT

The invention provides a marine antifouling coating composition comprising a tributyltin acrylate coresin in the range of from about 10% to about 25% by weight, a tributyltin polysiloxane coresin in the range of from about 2% to about 20% by weight, at least one filler in the range of from about 10% to about 50% by weight and a solvent in an amount of from about 20% to about 50% by weight. Preferred tributyltin acrylate coresins comprise copolymers of tributyltin methacrylate monomers and methyl methacrylate monomers.

35 Claims, No Drawings

ORGANOTIN ACRYLATE AND ORGANOTIN POLYSILOXANE ANTIFOULING COATING COMPOSITION

FIELD OF THE INVENTION

This invention relates to marine antifouling coating compositions including organotin acrylate and organotin polysiloxane coresins in a paint mixture.

BACKGROUND OF THE INVENTION

When a ship moves through the water the drag resistance or water frictional forces which must be overcome are responsible for as much as half of the power consumed in operation of the vessel. The surface condition of the hull is a major factor inducing drag. It is therefore desirable to have an extremely smooth surface on the hull and paint formulations have been developed that are very smooth when cured and/or are polished by moving water to provide an extremely smooth surface. It is desirable to have a coating material that exhibits this polishing action to produce a microsmooth surface to minimize the drag penalty due to microroughness.

Fouling of the hull by pestiferous marine organisms is a major source of drag. The use of antifouling protective coatings on a ship's hull is a primary approach to controlling fouling and the resulting drag. The antifouling coating inhibits growth of marine organisms on the hull to keep it smooth. Coatings can also be used on static structures exposed to seawater to minimize growth of organisms that could cause deterioration of such structures.

A truly effective antifouling coating meets at least three criteria: (1) it will possess broad spectrum antifouling efficacy (i.e., inhibit growth of a broad variety of organisms) for extended periods of time, usually three years; (2) it will possess a smooth surface so as not to cause a microroughness drag penalty; and (3) it will actively reduce drag by reducing the roughness profile of the surface.

To meet the first criterion it is necessary to deliver to the surface of the coating in a controlled fashion, minimum effective amounts of toxin or fouling control agents. The amount of toxin delivered at the surface should not be substantially above the minimum effective amount for inhibiting fouling to avoid premature depletion of the antifouling agent.

One technique for controlling release of toxin involves the use of latent toxicants which are activated by an environmental or chemical trigger such as hydrolysis. This is the principle behind the operation of organotin acrylate copolymers as described in U.S. Pat. No. 3,167,473. In these materials a trisubstituted organotin moiety is chemically bonded to a macromolecular acrylate backbone. At the surface of the coating, the organotin moiety is liberated by hydrolysis as an active fouling control agent.

Upon hydrolysis of the organotin ester groups, the acrylate copolymer increases in hydrophilicity because of the incipient production of carboxylic acid groups in the chain. As a consequence, the acrylate copolymer loses integrity such that the outermost molecular layer of the acrylate "polishes" under dynamic conditions. By this ablation mechanism underlying organotin ester groups are eventually exposed and liberated at the surface of the coating. However, as a result of the turbulence requirement, the antifouling performance of organotin acrylate coplymers in static media is marginal.

Further, organotin acrylate copolymer films, while having a desirable smooth surface and exhibiting turbulent polishing properties, have poor integrity and require the addition of ablation control agents to control premature or uncontrolled dissolution. Even so, service life is a function of film thickness and to achieve targeted service life, very thick coatings must be used in multiple coats. This increases materials and application costs and fixes an upper limit on practical use life.

SUMMARY OF THE INVENTION

It has been found that organotin siloxane polymers in certain concentrations are compatible with organotin acrylate copolymers and can be hydrolyzed and condensed in situ to form a three dimensional reinforcing matrix interpenetrating the organotin acrylate copolymer to control the dissolution and hardness of the composition. Further, the organotin siloxane polymers enhance the antifouling performance of the composition in static media. There is, therefore, provided in practice of this invention a marine antifouling coating composition comprising an organotin acrylate copolymer in the range of from about 10 to 25% by weight, an organotin polysiloxane in the range of from about 2 to 20% by weight, a solvent for the organotin acrylate copolymer and organotin polysiloxane in the range of about 20 to 50% by weight with the balance of the composition in the range of from about 10 to 50% by weight being primarily conventional marine paint fillers and/or pigments.

It is particularly preferred that the composition also includes copper or copper salts that are effective for inhibiting growth of marine organisms and facilitating the release of toxins by controlling the seawater sensitivity of the film, zinc oxide to enhance the transport of copper ions across biological membranes in marine organisms, a plasticizer to impart flexibility and resilience to the cured composition, an anti-settling agent for maintaining the insoluble solids in suspension, a viscosity stabilizing agent, and/or an algicide.

DETAILED DESCRIPTION

The marine antifouling coating composition provided in practice of this invention comprises a mixture of resins or binder, solvent and pigments or fillers, along with associated marine paint and antifouling ingredients in a consistency suitable as a paint for brushing, spraying, or the like on ship hulls or other structures exposed to seawater.

The binders in the composition comprise an organotin acrylate coresin in the range of from about 10 to 25% by weight and an organotin polysiloxane coresin in the range of from about 2 to 20% by weight. A volatile organic solvent for the organotin acrylate and organotin polysiloxane coresin is preferably present in the range of from about 20 to 50% by weight. The balance of the composition in the range of from about 10 to 50% by weight comprises conventional plasticizers, pigment powders, fillers, thickening agents, copper powder, copper salts, zinc oxide, algicides, clay, talc, metal oxides and the like.

It is particularly desirable that the composition include copper powder of cuprous salts that are effective for inhibiting growth of marine organisms. Preferably the copper or cuprous salt is present in a proportion of up to about 50% by weight.

The organotin acrylate coresin comprises at least one polymeric precursor having the formula:

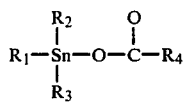

wherein $R_1$, $R_2$ and $R_3$ are each independently selected from the group consisting of alkyl, cycloalkyl and aryl radicals, collectively containing up to 18 carbon atoms and $R_4$ is a polymerizable radical selected from the groups consisting of vinyl, α-methylvinyl and vinylphenyl radicals. It is preferred that the organotin moiety of the organotin acrylate monomer be a tributyltin radical for optimum toxicity of the composition to marine organisms. The organotin acrylate coresin may be a homopolymer of an organotin acrylate monomer having the above formula, copolymers of two or more such organotin acrylate monomers or copolymers of one or more such organotin acrylate monomers and one or more ethylenically unsaturated monomers. Suitable organotin acrylate monomers and ethylenically unsaturated monomers for use in this invention are described in U.S. Pat. No. 3,167,473 to Leebrick which is incorporated herein by reference.

The presently preferred organotin acrylate coresins include Biomet 300, 302, 303 and 304, all manufactured by M & T Chemicals, Inc., Rahway, N.J. These coresins are all copolymers of a tributyltin methacrylate monomer and methyl methacrylate monomer. The percentage of tributyltin methacrylate monomers in these products ranges generally from about 59% to about 64% and are preferred because of their performance and commercial availability.

The organotin polysiloxane coresin comprises at least one polymeric percursor having the formula:

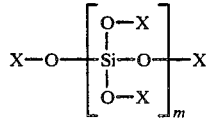

where m is in the range up to an average of about 10 and preferably an average of at least about 5. In this formula each X is independently selected from the group consisting of $R_5$ and Y. Each $R_5$ is selected from the group consisting of hydrogen, and alkyl and alkoxyalkyl radicals containing less than six carbon atoms. Each Y in the formula is a trisubstituted organotin radical having the formula:

In this organotin moiety $R_6$, $R_7$ and $R_8$ are independently selected from the group consisting of alkyl, cycloaklyl, and aryl radicals and collectively contain up to about 18 carbon atoms.

It is presently preferred that the Y's in the organotin polysiloxane polymeric precursor be tributyltin radicals and that the $R_5$'s be hydrogen or ethyl radicals.

In the polysiloxane, m represents the average number of silicon atoms per molecule. Generally there is a random distribution of molecules having more or less than m silicon atoms. For example, when m=5, molecules containing 4, 5 and 6 silicon atoms can be present. Preferably, m is less than about 10 so that the siloxane can be properly polymerized by hydrolysis and polycondensation during curing of the coating composition.

Preferably m is an average of about 5. Such a polysiloxane can polymerize, following transesterification to introduce the organotin moiety, to produce linear and/or cross-linked polymers. Such material has a high silica content, hence a relatively high proportion of solid binder following polycondensation and removal of the preferred ethyl radical. The character of the organotin siloxane polymer is determined by the ratio of organotin moieties to siloxane moieties, and hence the ratio of tin atoms to silicon atoms. Generally, the greater the amount of organotin moieties, the greater the organic character of the polymer, and the greater the compatibility with the organotin acrylate polymer. Conversely, the lesser the amount of organotin moieties, the greater the inorganic character of the polymer, and the lesser the compatibility with the organotin acrylate polymer.

It is preferred that the X's in the formula be selected so that the ratio of tin atoms to silicon atoms in the organotin polysiloxane is in the range of from about 1.7:5 to 5:5.

If the ratio of tin atoms to silicon atoms in the composition is less than about 1.7 tin atoms for every 5 silicon atoms, the character of the organotin siloxane polymer is insufficiently organic to be compatible with the organotin acrylate copolymer. Further, the quantity of the organotin moiety is so low that the contribution to the toxicity of the coating to marine organisms from organotin polysiloxane is marginal.

The proportion of tin atoms to silicon atoms in the organotin polysiloxane component should be less than about 5:5 for polymerization of the polysiloxane. The trisubstituted tin moiety on the polysiloxane introduces sufficient steric hindrance that at high tin to silicon ratios cross-linking is inhibited. Thus, with high tin to silicon ratios, the mechanical properties of the polymerized siloxane are reduced. Preferably, the tin to silicon ratio in the polysiloxane is about 2.5:5. A composition having a ratio of about 2.5 tin atoms for every 5 silicon atoms in the polysiloxane forms an excellent binder for the coating composition with sufficient organotin moiety for high toxicity of marine organism. Such a material has about the optimum balance of mechanical properties and toxicity.

Organotin polysiloxane polymeric precursors suitable for use in the present composition and methods for making them are disclosed in U.S. Pat. Nos. 4,080,190 and 4,385,134 which are both incorporated herein by reference.

It will be recognized that the quantity of organotin polysiloxane binder in the composition following hydrolysis and condensation will be less than the proportion of organotin siloxane in the uncured coating composition. For example, when the organotin siloxane comprises a tributyltin moiety on an ethoxy siloxane wherein each molecule has an average of five silicon atoms and the ratio of tin to silicon atoms is about 2.5:5, the cured siloxane has about 73% of the weight of the uncured precursor. The weight loss comes about from loss of the ethyl radical upon hydrolysis and condensation.

The organotin acrylate and organotin polysiloxane polymers in the composition act as coresins forming a binder for a paint coating. Evaporation of the solvent from the composition and exposure of the composition to environmental water or water vapor results in solidification of the binder blend through concurrent hydrolytic polycondensation of the acrylate and siloxane. The solidified binder system is in the form of an interpenetrating polymer network.

Preferably, the organotin acrylate coresin is present in the composition in the range of from about 10 to 25% by weight. If the proportion is less that about 10% by weight, the beneficial "polishing" effect of the organotin acrylate coresin is lost. This results in increased surface roughness of the composition surface, and a concomitant increase in drag. Also, since the organotin acrylate coresin is the major source of the antifouling organotin moiety, a proportion of less than about 10% by weight provides a quantity of organotin moiety which can become so low that the antifouling characteristics of the composition can be too low for practical use.

If the proportion of organotin acrylate coresin in the composition is more than about 25% by weight, the mechanical properties of the organotin acrylate coresin can predominate over those of the organotin polysiloxane coresin, thereby reducing the desirable properties of the organotin polysiloxane. Further, high proportions of organotin acrylate coresin can reduce the content of other toxicants such as copper bearing antifouling agents, thereby narrowing the spectrum of organisms against which the antifouling coating is effective.

The organotin polysiloxane is preferably present in the composition in the range of from about 2 to 20% by weight. If the proportion is less than about 2% by weight, the composition is insufficiently hard and the "polishing" effect of the organotin acrylate coresin remains uncontrolled. Further, the quantity of the organotin moiety in the organotin polysiloxane can become so low that the antifouling characteristics of the composition in static media can be undesirably low. The rate of release of toxicant at the coating surface can be less than the minimum required for inhibiting growth of organisms.

If the proportion of organotin polysiloxane coresin in the composition is more than about 25% by weight, the mechanical properties of the organotin polysiloxane predominate over the organotin acrylate coresin, thereby reducing the desirable "polishing" effect of the organotin acrylate. As with the organotin acrylate coresin, high proportions of the organotin polysiloxane coresin can reduce the content of other toxicants, such as copper-bearing, antifouling agents, thereby narrowing the spectrum of organisms against which the antifouling coating is effective.

Preferably the organotin acrylate coresin is present in the composition in an amount of from about 17 to about 25% by weight and the organotin polysiloxane coresin is present in an amount of from about 5 to about 15% by weight. These amounts provide a good balance of the polishing properties of the acrylate and the mechanical properties of the siloxane. Such a coating has a long useful lifetime and provides excellent antifouling performance in both static and dynamic conditions.

In the cured composition, the organotin acrylate in the binder provides a microsmooth surface that minimizes microroughness drag penalty, and a slow controlled polishing action can be obtained for providing maximum reduction of drag. In the preferred embodiment of this invention, the surface profile roughness envelope is in the 15 to 25 micron range throughout the service life of the coating and its ablative rate is less than 3 microns of coating loss per month at a speed of 15 knots.

The organotin moiety of the organotin acrylate is released as a result of the controlled dissolution of the acrylate. Since the dissolution or "polishing" of the acrylate occurs to a greater extent under dynamic conditions, the release of organotin moiety occurs at a greater rate under dynamic conditions.

The organotin moiety of the organotin polysiloxane is released by hydrolysis from the polysiloxane. Since it is not free to migrate or diffuse before hydrolysis, and since the rate of hydrolysis remains generally steady throughout the life of the coating, the rate of release of the organotin moiety from the organotin polysiloxane is generally steady throughout the life of the coating.

An organic solvent for the organotin acrylate and organotin polysiloxane is present in the range of from about 20 to 50% by weight. Xylene is an excellent solvent for both the organotin acrylate and the organotin polysiloxane. Other nonpolar solvents for organotin acrylates and polysiloxane can also be used, along with limited amounts of alcohols. Exemplary solvents are xylene, toluene, various Cellosolves, naphtha and mineral spirits. The organic solvents should be selected to provide a volatility that permits drying of the coating composition in a reasonable time when applied to the hull of a vessel or other substrate.

The proportion of solvent in the composition is subject to rather wide variation and is determined largely by the desired viscosity in the composition to permit application to substrates by spraying, brushing, or the like. If the proportion of solvent is less than about 20% by weight, the viscosity of the composition may be so high that application to substrates in coatings of reasonable thickness is rather difficult. Leveling to obtain a smooth coating may be inhibited. If the composition has more than about 50% by weight of solvent, application of coatings of reasonable thickness can be limited by sagging or running. Preferably, the solvent is present in the range of from about 25 to 45% by weight. It is found that such a proportion of solvent with the preferred resin compositions and other marine paint additives hereinafter described provides a viscosity range quite suitable for application to substrates by brushing and/or spraying.

A variety of other ingredients form the balance of the composition in the range of from about 10 to 50% by weight and preferably in the range of from about 28 to 48% by weight. Such additional ingredients are conventional additives to marine paints and are employed for modifying the properties of the coating composition or providing additional antifouling toxicity.

Among the other ingredients is at least one filler and/or pigment. Such materials modify the properties of the paint as it is applied, such as body to promote good spreading and leveling without runs or sags. Such materials also modify properties of the cured coating such as strength, toughness, opacity and color. Pigments and fillers also help protect the substrate on which the coating composition is placed. Exemplary pigments and fillers include iron oxide, talc, silicondioxide, titanium dioxide, chromium oxide, and the like.

Such pigments and fillers are to be included in the composition in the range of from about 10 to about 50% by weight. Preferably the pigments and fillers are present in the range of from about 17 to 27% by weight which provides good protection for substrates, opacity and strength.

In addition to the organotin acrylate and organotin polysiloxane, other marine antifouling ingredients can be included in the composition. In particular it is found desirable to include up to about 30% by weight of copper powder and/or cuprous salts, such as $Cu_2O$, CuSCN, $Cu_2S$, CuOH, or the like in the composition. Cuprous oxide is a preferred copper base antifouling agent. Such copper based materials are widely recognized as agents for inhibiting growth of marine organisms and are desirable additives in the marine coating composition. Preferably such copper base antifouling agents are present in the composition in the range of from about 4 to 8% by weight.

It is desirable to include copper bearing antifouling agents in the composition for enlarging the spectrum of marine organisms combatted by the antifouling coating. Copper and cuprous salts tend to be somewhat more effective for inhibiting growth of algae and more primitive soft organisms, whereas the organotin moiety is somewhat more effective against higher organisms, barnacles or the like, which are often referred to as "hard" fouling. When the proportion of copper base antifouling agent is in the range of from about 4 to 8% by weight, good longlife antifouling characteristics are obtained without decreasing other desirable properties of the coating.

When a copper based antifouling agent is included in the composition, it is also desirable to include zinc oxide in a proportion of about one-half the proportion of copper base antifouling agent. The zinc oxide is desirable since it potentiates the antifouling activity of the copper by enhancing the transport of copper ion across the biological membranes or marine organisms. Zinc oxide can also promote galvanic release of copper from the antifouling coating. An excess amount of zinc oxide can suppress the antifouling activity of the copper, hence, it is desirable that the maximum zinc oxide be in a proportion of about 50% of the copper base antifoulant. If zinc is included in the composition, the proportion of zinc oxide should be reduced.

It is believed that no single toxicant is available for compositions that can be applied to surfaces in practical situations and that will universally protect marine surfaces against fouling. While organotin compounds are very effective as antifouling toxicants, practical compositions that provide controlled release of toxicant over long periods of time do not have sufficently broad antifouling properties for the full spectrum of organism. It is found, however, that by combining the organotin acrylate with an organotin polysiloxane and with other toxicants, such as copper or cuprous salts or organic algicides, the antifouling performance of the coating can be effective in a wide variety of fouling environments for periods of time far in excess of conventional coatings. This effectiveness is present under both static and turbulent conditions. This differs from prior compositions for controlled release of toxicants which are optimized for either static or dynamic conditions, rather than both.

It is particularly advantageous to employ copper-bearing, antifouling agents such as copper powder or cuprous salts as an additional toxicant in a coating composition having organotin acrylate and organotin polysiloxane binders, because such a binder system appears to stabilize the copper or copper compounds. Ordinarily in a seawater environment at least a portion of the copper is converted to inactive salts, such as copper oxychlorides, which are relatively ineffective in inhibiting growth of marine fouling organisms. The reason that the organotin acrylate and organotin polysiloxane binders tend to stabilize the copper or copper salts in seawater is not yet understood. It is believed that since the composition contains organotin moieties, the amount of copper-bearing, antifouling agent can be reduced, as compared with prior compositions, without reducing antifouling activity, and that the lower copper concentration may avoid passivation.

Preferably, the composition includes a conventional plasticizer for the binders in an amount of up to about 5% by weight, and most preferably in the range of from about 1 to 3% by weight. The plasticizer imparts flexibility and resilience to the cured composition. External plasticizers that maintain their molecular identity are preferred, rather than plasticizers that chemically bond in the polymer system. A variety of conventional plasticizers that are compatible with the organotin acrylate and organotin polysiloxane are suitable, such as alkyl benzyl, phthalates, dialkyl phthalates, phosphate esters, sulfonamides, butylphthalylbutyl glycolate, diphenyl phthalate, dicyclohexyl phthalate, tricresyl phosphate, and the like. Di-isodecylphthalate is presently preferred.

It is highly desirable to include a viscosity stabilizing agent. Such viscosity stabilizing agents are in paint compositions for modifying viscosity and obtaining paints that can be sprayed or brushed to provide a coating of reasonable thickness without sagging or running. An exemplary viscosity stabilizing agent particularly useful is Viscostab available from M & T Chemicals, Inc., Rahway, N.J. Preferably the viscosity stabilizer is present in the composition in the range of from about 6 to 20% by weight and most preferably in the range of from about 6 to 10% by weight, as is conventional in such paint compositions.

It is desirable to include antisettling agents for the copper base materials and other fillers and pigments employed in the composition. A variety of antisettling agents used in paint compositions are suitable for preventing settling and minimizing mixing that might be needed before a composition is used after a prolonged shelf life. Antisettling agents are employed in marine paint compositions up to about 3% by weight and preferably in the range of from about 1 to 3% by weight.

If desired, organic algicides can be included in the composition, such as dichloroisothiazalone or diiodomethyl p-tolyl sulfone. Preferably, such algicides are present in a proportion up to about 16% by weight, and most preferably in the range of from about 3 to 13% by weight. Such algicides can promote gelling of the composition and the proportions are preferably kept low enough to inhibit such gelling and maintain a long shelf life.

The proportions of liquid and solid ingredients are selected so that the composition can be sprayed or brushed onto a variety of substrates as a marine paint. The composition is preferably packaged in a single container for ready use as a paint. If desired it can be prepared in two packages for longer shelf life and mixed shortly before use. Many other modifications and variations will be apparent.

When the coating composition is applied to a surface, concurrent effects are occurring in the acrylate and polysiloxane binders. The organotin acrylate resin forms a solid binder network as the volatile solvents evaporate. The organotin polysiloxane hydrolyzes and condenses in situ. If desired, the polysiloxane can be at least partially hydrolyzed in a solvent before blending with the acrylate. Such prehydrolysis can be desirable for rapid cure of the coating, but the shelf life of the mixture may be decreased.

Hydrolysis of the polysiloxane can occur from ambient water vapor or exposure to water. A variety of bases or acids can be present in small quantities to promote hydrolysis as described in U.S. Pat. No. 4,080,190. Algicides, zinc oxide and other ingredients in the composition can be sufficient to promote hydrolysis. It might be noted that use of some basic promoters of hydrolysis may not be totally compatible with copper-bearing, antifouling agents. Such promoters may be omitted or the composition used within a reasonable time after mixing, or the copper bearing materials can be added shortly before applying the coating.

Dilute aqueous hydrochloric acid can be used to catalyze the hydrolysis and condensation of the precursor. Other acids which can be used as catalysts include mineral acids such as sulfuric acid, orthophosphoric acid, and nitric acid, and organic acids such as trichloroacetic acid, formic acid and oxalic acid. The amounts to be used vary for each acid, but the optimum quantity can readily be determined by a chemist of ordinary skill in the art. The action of organic acids generally is slower than that of inorganic acids. Therefore, a binder catalyzed with an organic acid preferably is immersed in or sprayed with water after the binder has set to help the coating attain its final hardness.

A solvent for the precursor may be used to aid in acid catalyzed hydrolysis. Preferably a volatile solvent is used so that quick drying of a coating formed from the precursor occurs. Exemplary of solvents which can be used are acetone, isopropanol, pentanone, and methylisobutyl ketone, which is preferred because it seems to stabilize the hydrolyzed precursor.

Hydrolysis of the precursor can also be catalyzed by a hydroxyl source which itself is nonreactive with the precursor but which reacts with moisture to produce hydroxyl ions, such as described in U.S. Pat. No. 3,653,930, issued to Law et al, assigned to the assignee of this invention, and incorporated herein by reference. This patent describes catalyzing hydrolysis of silicates with a hydroxyl source nonreactive with the silicate and reactive with moisture to produce hydroxyl ions. Exemplary of hydroxyl sources disclosed in U.S. Pat. No. 3,653,930 are organic sources such as amines such as mono-, di- and triethanolamine, diamylamine, cyclohexylamine piperidine, and the like, and inorganic hydroxyl sources such as potassium, sodium and lithium hydroxide.

EXAMPLES

Table I sets forth the compositions of five antifouling coating compositions prepared in practice of this invention. The compositions were mixed much as one would mix other paint compositions. The compositions were applied to standard test panels to a thickness of about 250 microns (10 mils) by spraying and the test panels were immersed in seawater at Daytona Beach, Fla., for determining antifouling activity.

TABLE I

| Ingredient | Examples | | | | |
|---|---|---|---|---|---|
| | A | B | C | D | E |
| BioMet 300 | 47.98 | 41.85 | 47.94 | — | — |
| BioMet 302 | — | — | — | 41.81 | — |
| BioMet 303 | — | — | — | — | 41.81 |
| High Flash Naptha | 3.00 | 3.58 | 3.08 | 3.59 | 3.59 |
| Mineral Spirits | 5.35 | 8.53 | 5.37 | 8.60 | 8.60 |
| Titanium Dioxide | 37.81 | 29.94 | 14.48 | 30.00 | 30.00 |
| C-9211 | 5.86 | 5.85 | 7.10 | 6.00 | 6.00 |
| AO-525 | — | — | 21.32 | — | — |
| AO-525B | — | 10.25 | — | 10.00 | 10.00 |
| Ethyl Aminoethanol | — | — | 0.71 | — | — |
| Total | 100.0 | 100.0 | 100.00 | 100.00 | 100.00 |

The proportions of ingredients listed in Table I are set forth in percentages by weight for each of the coating compositions. The materials set forth in Table I are identified as follows:

BioMet 300, 302 and 303 solutions contain copolymers of tributyltin methacrylate and methyl methacrylate in high flash naptha and are available from M & T Chemicals, Inc., Rahway, N.J. The solutions have approximately 50% by weight polymer. In BioMet 300, the polymer typically has a molecular weight of about 52,000 and comprises approximately 64% by weight tributyltin methacrylate monomers and 36% by weight methyl methacrylate monomers. In BioMet 302, the polymer typically has a molecular weight of about 55,000 and comprises approximately 65% by weight tributyltin methacrylate monomers and 35% by weight methyl methacrylate monomers. The polymer in BioMet 303 also has a tyical molecular weight of 55,000 and comprises about 63.5% by weight tributyltin methacrylate monomers and 36.5% by weight methylmethacrylate monomers.

C-9211 is a 4,5-dichloro-2-n-octyl-3(2H)-isothiazolone algicide available from Rohm and Haas Company, Philadelphia, Pa. The algicide can also provide a source of protons to promote hydrolysis of the siloxane. It is desirable in preparing a composition to add the algicide after all of the other ingredients have been mixed to minimize the possibility of premature gelation.

AO-525 is an organotin polysiloxane prepolymer prepared as described in U.S. Pat. No. 4,080,190 with 40% hydrolyzed ethyl silicate and a tributyltin compound in amounts sufficient to generate a ratio of about 5 silicon atoms to each 2.5 tin atoms in the precursor.

AO-525B is a solution containing a 100% hydrolyzed tributyltin polysiloxane in a solvent. The amount of tributyltin polysiloxane is about 87.2% by weight, the rest being solvent, specifically xylene.

The composition was prepared by mixing the organotin acrylate, the organotin polysiloxane and the solvent. After all of the liquid and soluble materials have been mixed, the titanium dioxide was added with as much mixing shear as required to obtain a smooth paint composition. The algicide was then added, followed, in Example C, by the amine catalyst. The order of adding ingredients to the composition is not critical, although it is desirable to add the algicide or any catalyzing amine last in order to minimize premature gelation.

The coating compositions set forth in Table I were applied to standard blank panels of primer-coated steel or plastic for measuring resistance to marine fouling. The ablation properites of these compositions are set forth in Table II below.

TABLE II

| Example | Hardness | Use Life (months) | Approximate Ablation Rate (microns/day @15 Knots) |
|---------|----------|-------------------|---------------------------------------------------|
| A | Soft | 16 | 0.5 |
| B | Moderate | 20–28 | 0.3–0.4 |
| C | Firm | 28–41 | 0.2–0.3 |
| D | Hard | 28–54 | 0.15–0.3 |
| E | Hard | 28–54 | 0.15–0.3 |

Ablation rates were determined by mounting a panel on a disk and rotating the disk at a circumferential speed of 15 knots under sea water.

These panels were exposed to seawater at San Pedro, Calif. The fouling resistance of the compositions as a function of months of exposure as set forth in Table III.

TABLE III

| EXAMPLE | HARD FOULING | | | | | ALGAL FOULING | | | | |
|---------|---|---|---|---|---|---|---|---|---|---|
| | 6 | 12 | 18 | 24 | 30 mos. | 6 | 12 | 18 | 24 | 30 mos. |
| A | 10 | 10 | 10 | 10 | 9 | 10 | 10 | 10 | 9 | 8 |
| B | 10 | 10 | 10 | 10 | 9 | 10 | 10 | 9 | 8 | 8 |
| C | 10 | 10 | 10 | 10 | 10 | 10 | 10 | 10 | 9 | 9 |

Hard fouling refers to the growth of barnacles and similar organisms with hard body parts. Algal fouling refers to algae and other soft organisms. The ratings of the test panel for fouling resistance is on a scale of 0 to 10, where 10 represents no fouling whatsoever, 9 represents a very minor or trace amount of fouling, 5 represents approximately 50% of the test panel fouled and 0 represents complete failure or fouling over the entire surface.

What is claimed:

1. A marine antifouling coating composition comprising:

an organotin acrylate coresin comprising at least one polymeric precursor having the formula

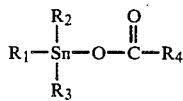

where $R_1$, $R_2$ and $R_3$ are independently selected from the group consisting of alkyl, cycloalkyl and aryl radicals and $R_1$, $R_2$ and $R_3$ collectively contain up to 18 carbon atoms and where $R_4$ is a polymerizable radical selected from the group consisting of vinyl, α-methylvinyl and vinylphenyl radicals, the organotin acrylate coresin being in the range of from about 10 to about 25% by weight;

an organotin polysiloxane coresin comprising at least one polymeric precursor having the formula

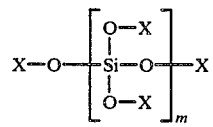

where m is an average of up to about ten, each X is independently selected from the group consisting of $R_5$ and Y; where each $R_5$ is selected from the group consisting of hydrogen and alkyl and alkoxyalkyl radicals containing less than six carbon atoms; where each Y is a trisubstituted tin radical having the formula

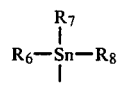

where $R_6$, $R_7$ and $R_8$ are independently selected from the group consisting of alkyl, cycloalkyl and aryl radicals and $R_6$, $R_7$ and $R_8$ contain collectively up to 18 carbon atoms; the organotin polysiloxane coresin being in the range of from about 2 to about 20% by weight;

solvent for the organotin acrylate and organotin polysiloxane coresin in the range of from about 20% to about 50% by weight; and the balance in the range of from about 10% to about 50% by weight comprising marine paint and toxicant agents selected from the group consisting of pigment powders, fillers, plasticizers, antisettling agents, copper powder, cuprous salts, zinc oxide and algicides.

2. A marine antifouling coating composition as claimed in claim 1 wherein $R_1$, $R_2$ and $R_3$ are each butyl.

3. A marine antifouling coating composition as claimed in claim 1 wherein $R_6$, $R_7$ and $R_8$ are each butyl.

4. A marine antifouling coating composition as claimed in claim 1 wherein $R_5$ is selected from the group consisting of hydrogen and ethyl radicals.

5. A marine antifouling coating composition as claimed in claim 1 wherein the organotin acrylate coresin is present in an amount of from about 17% to about 25% by weight.

6. A marine antifouling coating composition as claimed in claim 1 wherein the organotin polysiloxane is present in an amount of from about 5% to about 15% by weight.

7. A marine antifouling coating composition as claimed in claim 1 wherein the ratio of tin atoms to silicon atoms in the organotin polysiloxane polymeric precursor is from about 1.7:5 to about 5:5.

8. A marine antifouling coating composition as claimed in claim 7 wherein the ratio of tin atoms to silicon atoms in the organotin polysiloxane polymeric precursor is about 2.5:5.

9. A marine antifouling coating composition as claimed in claim 1 wherein the solvent is present in an amount of from about 25% to about 45% by weight.

10. A marine antifouling coating composition as claimed in claim 1 wherein the composition comprises a toxicant selected from the group consisting of copper salts and mixtures thereof in an amount of up to about 50% by weight.

11. A marine antifouling coating composition as claimed in claim 1 wherein the composition comprises a plasticizer in an amount of up to about 5% by weight.

12. A marine antifouling coating composition as claimed in claim 1 wherein the composition comprises zinc oxide in an amount up to about 15% by weight.

13. A marine antifouling coating composition as claimed in claim 1 wherein the composition comprises an antisettling agent in an amount of up to about 3% by weight.

14. A marine antifouling coating composition as claimed in claim 1 wherein the composition comprises an algicide in an amount of up to about 16% by weight.

15. A marine antifouling coating composition as claimed in claim 1 wherein the composition comprises a filler or pigment powder selected from the group consisting of iron oxide, talc, titanium dioxide, silicon dioxide, and chrome dioxide and mixtures thereof.

16. A marine antifouling coating composition as claimed in claim 1 wherein the filler or pigment powder is present in the range of from about 10% to about 50% by weight.

17. A marine antifouling coating composition as claimed in claim 1 wherein the organotin polysiloxane is hydrolizable in situ.

18. A marine antifouling coating composition as claimed in claim 1 wherein the organotin polysiloxane is partially prehydrolized.

19. A marine antifouling coating composition as claimed in claim 1 wherein the organotin acrylate coresin comprises copolymers of tributyltin methacrylate monomers and methyl methacrylate monomers.

20. A marine antifouling coating composition comprising:
an organotin acrylate coresin comprising at least one polymeric precursor having the formula:

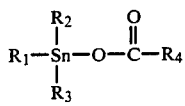

where $R_1$, $R_2$ and $R_3$ are each butyl and where $R_4$ is a polymerizable radical selected from the group consisting of vinyl, α-methylvinyl and vinylphenyl radicals, the organotin acrylate coresin being in the range of from about 10 to about 25% by weight;
an organotin polysiloxane coresin comprising at least one polymeric precursor having the formula:

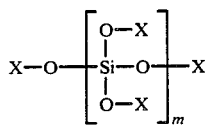

where m is an average of up to about 10, each X is independently selected from the group consisting of hydrogen and ethyl radical, where each Y is a tributyltin radical and the X's are selected so that the ratio of tin atoms to silicon atoms is in the range from 1.7:5 to 5:5, the organotin polysiloxane being present in the range of from about 2 to about 20% by weight;
a solvent for the organotin acrylate and organotin polysiloxane in an amount of from about 20% to about 50% by weight; and
a filler or pigment powder selected from the group consisting of iron oxide, talc, silicon dioxide, titanium dioxide, chromium oxide and mixtures thereof in an amount of from about 10% to about 50% by weight.

21. A marine antifouling coating composition as claimed in claim 20 wherein the organotin acrylate coresin comprises copolymers of tributyltin methacrylate monomers and methyl methacrylate monomers.

22. A marine antifouling coating composition as claimed in claim 20 wherein the organotin acrylate coresin is present in an amount of from about 17% to about 25% by weight.

23. A marine antifouling coating composition as claimed in claim 20 wherein the organotin polysiloxane coresin is present in an amount of from about 5% to about 15% by weight.

24. A marine antifouling coating composition as claimed in claim 20 wherein the ratio of tin atoms to silicon atoms in the organotin polysiloxane polymeric precursor is about 2.5:5.

25. A marine antifouling coating composition as claimed in claim 20 wherein the solvent is present in an amount of from about 25% to about 45% by weight.

26. A marine antifouling coating composition as claimed in claim 20 wherein the composition further comprises a toxicant selected from the group consisting of copper salts and mixtures thereof in an amount of up to about 50% by weight.

27. A marine antifouling coating composition as claimed in claim 20 wherein the composition further comprises a plasticizer in an amount of up to about 5% by weight.

28. A marine antifouling coating composition as claimed in claim 20 wherein the composition further comprises zinc oxide in an amount up to about 15% by weight.

29. A marine antifouling coating composition as claimed in claim 20 wherein the composition further comprises an antisettling agent in an amount of up to about 3% by weight.

30. A marine antifouling coating composition as claimed in claim 20 wherein the composition further comprises an algicide in an amount of up to about 16% by weight.

31. A marine antifouling coating composition as claimed in claim 20 wherein the composition further comprises a viscosity stabilizing agent in the range of from about 6 to about 20% by weight.

32. A marine antifouling coating composition as claimed in claim 20 wherein the organotin polysiloxane is hydrolizable in situ.

33. A marine antifouling coating composition as claimed in claim 20 wherein the organotin polysiloxane is partially prehydrolized.

34. A marine antifouling coating composition comprising:
an organotin acrylate coresin comprising copolymers of tributyltin methacrylate monomers and methyl methacrylate monomers in the range from about 10% to about 25% by weight;
an organotin polysiloxane coresin comprising an organotin polysiloxane having a ratio of tin atoms to silicon atoms of from about 1.7:5 to about 5:5, said organotin polysiloxane coresin being present in the range of from about 2% to about 20% by weight;
a solvent for the organotin acrylate and organotin polysiloxane in an amount of from about 20% to about 50% by weight; and
the balance in the range of from about 10% to about 50% by weight comprising marine paint and toxicant agents selected from the group consisting of pigment powders, fillers, plasticizers, antisettling agents, copper powder, cuprous salts, zinc oxide and algicides.

35. A marine antifouling coating composition as claimed in claim 34 wherein the ratio of tributyltin methacrylate monomers to methyl methacrylate monomers is in the range of from about 1:2 to about 1:2.5.

* * * * *